US011318006B2

(12) United States Patent
Halamish et al.

(10) Patent No.: US 11,318,006 B2
(45) Date of Patent: May 3, 2022

(54) INJECTION APPARATUS

(71) Applicant: Target Point Technologies Ltd, Yokneam Illit (IL)

(72) Inventors: Asaf Halamish, Pardes Hanna-Karkur (IL); Gershon Goldenberg, Pardes Hanna-Karkur (IL)

(73) Assignee: pHi-Tech Animal Health Technologies Ltd., Airport City (IL)

( * ) Notice: Subject to any disclaimer, the term of this patent is extended or adjusted under 35 U.S.C. 154(b) by 445 days.

(21) Appl. No.: 16/285,865

(22) Filed: Feb. 26, 2019

(65) Prior Publication Data

US 2019/0183622 A1 Jun. 20, 2019

Related U.S. Application Data

(63) Continuation of application No. 15/108,872, filed as application No. PCT/IL2014/051133 on Dec. 30, 2014, now Pat. No. 10,258,445.
(Continued)

(51) Int. Cl.
*A61D 7/00* (2006.01)
*A61D 1/02* (2006.01)
(Continued)

(52) U.S. Cl.
CPC ............... *A61D 7/00* (2013.01); *A61D 1/025* (2013.01); *A61M 5/19* (2013.01); *A61M 5/20* (2013.01);
(Continued)

(58) Field of Classification Search
CPC .. A61M 2005/2013; A61M 2005/2073; A61M 2005/3267; A61M 2005/341; A61M 2205/18; A61M 2205/502; A61M 2205/505; A61M 2205/52; A61M 2205/581; A61M 2205/583; A61M 2205/8206; A61M 39/24; A61M 5/19;
(Continued)

(56) References Cited

U.S. PATENT DOCUMENTS 4,276,879 A 7/1981 Yiournas
4,673,395 A 6/1987 Phillips
(Continued)

FOREIGN PATENT DOCUMENTS

CA 2959162 3/2016
CN 1791440 A 6/2006
(Continued)

OTHER PUBLICATIONS

Office Action for Mexican Application No. MX/a/2016/008647, dated Nov. 7, 2019 (4 pages) (5 pages of translation).
(Continued)

*Primary Examiner* — Brandy S Lee
(74) *Attorney, Agent, or Firm* — Klarquist Sparkman, LLP

(57) ABSTRACT

An injection apparatus for injecting a medicament into a patient, the injection apparatus has a stationary head and a movable head that is movable with respect to the stationary head. A needle is attached to a needle holder that is held by the movable head and by the stationary head. When the movable head is urged rearwardly, a front edge of the needle moves forwardly with respect to a front face of the movable head.

20 Claims, 19 Drawing Sheets

Related U.S. Application Data

(60) Provisional application No. 61/964,235, filed on Dec. 30, 2013.

(51) Int. Cl.
*A61M 5/20* (2006.01)
*A61M 5/19* (2006.01)
*A61M 5/315* (2006.01)
*A61M 5/32* (2006.01)
*A61M 39/24* (2006.01)
*A61M 5/34* (2006.01)

(52) U.S. Cl.
CPC ........ *A61M 5/31546* (2013.01); *A61M 5/322* (2013.01); *A61M 5/3286* (2013.01); *A61M 39/24* (2013.01); *A61M 2005/2013* (2013.01); *A61M 2005/2073* (2013.01); *A61M 2005/3267* (2013.01); *A61M 2005/341* (2013.01); *A61M 2205/18* (2013.01); *A61M 2205/502* (2013.01); *A61M 2205/505* (2013.01); *A61M 2205/52* (2013.01); *A61M 2205/581* (2013.01); *A61M 2205/583* (2013.01); *A61M 2205/8206* (2013.01)

(58) Field of Classification Search
CPC .... A61M 5/20; A61M 5/31546; A61M 5/322; A61M 5/3286
See application file for complete search history.

(56) References Cited

U.S. PATENT DOCUMENTS

| | | |
|---|---|---|
| 4,717,383 A | 1/1988 | Phillips et al. |
| 4,985,015 A | 1/1991 | Obermann |
| 5,807,336 A | 9/1998 | Russo |
| 6,858,020 B2 | 2/2005 | Rusnak |
| 7,056,307 B2 | 6/2006 | Smith et al. |
| 8,029,469 B2 | 10/2011 | Ethelfeld |
| 8,529,522 B2 | 9/2013 | Cohen |
| 9,706,754 B2 | 7/2017 | Prescott et al. |
| 10,258,445 B2 | 4/2019 | Halamish et al. |
| 2001/0008961 A1 | 7/2001 | Hecker et al. |
| 2002/0183616 A1* | 12/2002 | Toews ............... A61M 5/007 600/432 |
| 2005/0043681 A1 | 2/2005 | Rusnak |
| 2005/0209569 A1 | 9/2005 | Ishikawa et al. |
| 2006/0135910 A1 | 6/2006 | Luther et al. |
| 2008/0114305 A1* | 5/2008 | Gerondale ........ A61M 5/31595 604/207 |
| 2008/0177223 A1 | 7/2008 | Johnston et al. |
| 2009/0018505 A1* | 1/2009 | Arguedas .......... A61M 37/0069 604/131 |
| 2009/0163860 A1 | 6/2009 | Patrick |
| 2009/0198215 A1* | 8/2009 | Chong ................ A61M 5/1413 604/506 |
| 2010/0130960 A1 | 5/2010 | Spire |
| 2012/0073515 A1 | 3/2012 | Chung et al. |
| 2014/0114258 A1 | 4/2014 | Day |
| 2015/0128873 A1 | 5/2015 | Prescott et al. |
| 2015/0174321 A1 | 6/2015 | Cohen |
| 2016/0101240 A1 | 4/2016 | Samson |
| 2016/0235512 A1 | 8/2016 | Miller et al. |
| 2016/0263321 A1 | 9/2016 | Eisele et al. |
| 2016/0296313 A1 | 10/2016 | Fleming et al. |
| 2016/0324613 A1 | 11/2016 | Halamish et al. |
| 2017/0197037 A1 | 7/2017 | Edwards |

FOREIGN PATENT DOCUMENTS

| | | |
|---|---|---|
| CN | 102105183 | 6/2011 |
| CN | 203208448 U | 9/2013 |
| CN | 104812334 A | 7/2015 |
| CN | 105682607 A | 6/2016 |
| CN | 107468372 | 12/2017 |
| CN | 106029004 B | 3/2018 |
| EP | 2285436 | 10/2015 |
| EP | 3089703 A1 | 11/2016 |
| GB | 2233234 | 7/2015 |
| WO | WO 2004/101060 | 11/2004 |
| WO | WO 2008/057223 | 5/2008 |
| WO | WO 2008/079824 | 7/2008 |
| WO | 2009/134577 | 11/2009 |
| WO | WO 2010/052579 | 5/2010 |
| WO | WO 2012/176029 | 12/2012 |
| WO | WO 2013/064475 | 5/2013 |
| WO | WO 2014/016807 | 3/2014 |
| WO | WO 2014/107766 | 7/2014 |
| WO | WO 2015/101981 | 7/2015 |
| WO | WO 2017/086807 | 5/2017 |
| WO | WO 2017/086924 A1 | 5/2017 |
| WO | WO 2018/092138 A1 | 5/2018 |
| WO | WO 2018/203203 A1 | 11/2018 |

OTHER PUBLICATIONS

Office Action for Israeli Application No. 246538, dated Dec. 12, 2019 (4 pages, translation incorporated into Office Action).
Office Action for Chinese Application No. 201880029105.6, dated Jun. 2, 2021 (24 pages, with English translation).
Office action for European Application No. EPC 14876301.4 dated Mar. 10, 2020 (3 pages).
Office action for Brazil Application No. BR112016015342, dated May 13, 2020 (3 pages).
International Search Report & Written Opinion, PCT/IB2020/053177, dated Jul. 19, 2020 (20 pages).
Extended European Search Report, dated Sep. 1, 2020, European Patent Application No. EPC 18794760.1, filed Apr. 28, 2018 (10 pages).
Office Action for Mexican Application No. MX/a/2016/008647, dated Jul. 19, 2019 (3 pages).
Machine translation of Office Action for Mexican Application No. MX/a/2016/008647, dated Jul. 19, 2019 (4 pages).
International Search Report & Written Opinion, PCT/IB2018/059883, dated Mar. 25, 2019 (12 pages).
International Search Report & Written Opinion, PCT/IB2018/052958, dated Aug. 12, 2018 (14 pages).
European Search Report, EP 14876301.4, dated Aug. 3, 2017 (3 pages).
Examination Report for European Application No. EP 18888570.1, issued by the European Patent Office dated Oct. 25, 2021 (13 pages).
Office action for Chinese Application No. 201880079657.8 (includes translation), dated Oct. 27, 2021 (13 pages).
Office action for Chinese Application No. 201880029105.6, dated Dec. 28, 2021 (includes translation) (20 pages).
Office action for Indian Application No. 201917048613, dated Feb. 17, 2022 (includes translation) (5 pages).
Office action for U.S. Appl. No. 16/667,405, dated Jan. 6, 2022 (27 pages).

* cited by examiner

INJECTION APPARATUS

CROSS-REFERENCE TO RELATED APPLICATION

This application is a continuation of U.S. patent application Ser. No. 15/108,872 filed Jun. 29, 2016, which is a National Stage Entry of PCT/IL2014/051133 filed Dec. 30, 2014, which claims the benefit of U.S. Provisional Patent Application 61/964,235 filed Dec. 30, 2013, all of which are incorporated herein by reference.

FIELD OF THE INVENTION

The present invention relates to the field of injectors for injecting animals, and more particularly to the field of automatic injectors for injecting a large number of animals, for example, poultry or fish.

BACKGROUND OF THE INVENTION

In the field of animal treatment it is often required to inject to the animal a large variety of medicaments, in a liquid substance form, that may include, e.g., medicines, vaccines, hormones, food supplements and the like. For a matter of convenience, the above described substances that have to be injected will hereinafter be called "medicament".

When it is required to inject a large number of animals (or "patients"), e.g., poultry, fish, sheep, goats, cattle, and the like, the injecting should be fast and efficient since there is a large number of individuals involved during each injecting process, typically, tens of thousands.

When injecting to a large number of individuals, it is common that the operator gets tired. In this situation, several malfunctions may occur:
1—The operator may accidentally inject to himself
2—The operator may inject when the needle did not penetrate yet into the patient.
3—The operator may inject when the needle did not penetrate to the desired depth into the patient.
4—The operator may inject after the needle has been removed from the patient.
5—The operator may inject only a portion of the required dose.
6—The operator may insert the needle into the patient in a wrong orientation.
7—The operator may inject twice to the same individual.

Furthermore, since there is a large number of individuals involved and the process is typically done very quickly, it is sometimes difficult or impossible to monitor the individuals that were actually injected. Moreover, it is impossible to monitor the individuals which received the full dose versus those who did not receive the full dose. It is understood that these kinds of malfunctions cause additional cost to the process and further complications, such as an outbreak of a plague, due to the individuals that were not properly injected.

Injection apparatuses for performing these tasks are known. US2009018505(A1) discloses a powered automatic injection device having a hand-held gun-shaped with a handgrip. The device has an internal motor that is powered by connection to a power source, such as AC current or DC battery. A pair of limit switches controls the delivery of the medicament by limiting the movement of a helical gear that moves a fitting in response to being powered by the internal motor. The helical gear transfers rotational motion from the electric motor into linear motion through a coupling attached to the helical gear.

GB2233234(B) discloses a portable jet injector for avian vaccination that may include two ejection chambers fed separately with different vaccine compositions for being administrated simultaneously to one bird.

WO2004/101060 discloses an injector assembly adapted to be carried by the operating person. Contact sensor and positioning sensor delivers information to a controller. The controller orders propelling means, a dosing unit, and the needle to automatically push the medical material. The apparatus can be provided with electronically or physical marker for recording.

U.S. Pat. No. 6,858,020 discloses an automatic repeater vaccinator apparatus for dispensing a predetermined volume of a fluid into an animal, and reloading after each volume of fluid is dispensed.

U.S. Pat. No. 8,529,522 discloses an injection apparatus having a removable needle cartridge, wherein the cartridge having a plurality of needles. Each of the needles is advanced into a deployment position by means of an advancer.

WO 2014/016807 discloses a mass vaccination device which can electronically control and deliver a measured amount of a vaccine thorough a needle.

US 2008/0177223 discloses an injection system that may deliver at least two fluid doses to a small bird by penetrating the skin of the recipient bird with at least one injection needle.

US 2005/0209569 discloses an injection device. After pressing the device against the body of a patient, a needle automatically protrudes from the device into the patient and is immediately removed from the patient, thereby reducing the pain of the patient during insertion and removing of the needle.

None of the cited references discloses a method to insert a needle at a predetermined required angle with respect to the avian skin, at the right insertion depth, at a linear line during insertion, and releasing the dose when the front edge of the needle is positioned at the required depth.

U.S. Pat. No. 3,964,481 discloses a device comprising a needle (13) that protrudes at an angle with respect to a retention plate (14). The device comprises a casing (1) which rests on the table through four stuck rubber legs (4). An operation system is separated from a control system. A needle (13) is connected, through guide means (6c), to a housing (6). The needle is protruding to the patient through an aperture (18) in the retention plate (14). In order to perform an injection, the caregiver person has to hold the bird with one hand, and, with the other hand to hold one of the bird's legs and abut it against a right-angled abutment or stop member (16) that is found on the retention plate in order to assure the correct position for the injection. At this stage, the person presses a push member (19) and the needle protrudes outwardly from the aperture and makes the injection. It is unclear how the person performs this task since both of his hands are already occupied as described above. He has to either release one of his hands for pressing the push member (19), or, he has to release one finger for pressing the push member, or, he has to press with the outer portion of his palm when the bird's leg is grabbed by his hand and abutted against the stop member (16). In any case, the operation of the device with living birds is cumbersome.

Disadvantages of the device of U.S. Pat. No. 3,964,481 are: (1) the device is stationary and not mobile, (2) the bird has to be held with both hands, (3) the operation of the injection is cumbersome, (4) the injection is not being done automatically and it has to be operated by the person, (5) the device cannot get to any bird, but, each of the birds has to be placed on the device, in the exact position, prior to operation of the needle.

It is the object of the present invention to provide an injection apparatus that significantly reduces or overcomes the aforementioned disadvantages.

It is a further object of the present invention to provide an injection apparatus that automatically injects into the animal when it is pressed against the animal.

It is still a further object of the present invention to provide an injection apparatus wherein its needle penetrates into the patient (e.g., poultry or fish) always at the correct desirable angle.

It is still yet a further object of the present invention to provide an injection apparatus wherein its needle moves along a straight line throughout the penetration into the patient.

It is also a further object of the present invention to provide an injection apparatus wherein its needle penetrates into the patient always at the exact desirable depth.

It is another object of the present invention to provide an injection apparatus wherein the treatment material is injected only after the needle has reached the desirable depth.

It is still yet another object of the present invention to provide an injection apparatus that provides full delivery of the treatment material into the patient.

It is still further another object of the present invention to provide an injection apparatus that prevents accidental exposure of the needle or accidental injection.

It is also another object of the present invention to provide an injection apparatus that provides easy and comfortable holding and an ergonomic grip by the entire operator's hand, and prevents from each of the operator's fingers, palm or wrist from becoming tired.

It is another object of the present invention to provide an injection apparatus that marks each patient been injected.

It is yet another object of the present invention to provide an injection apparatus that provides and transmits data regarding the injection process, e.g., number of proper injections, number of faulty injections, amount of injected medicament, rate of injections, intermissions, caregiver person's identifying code, etc.

SUMMARY OF THE INVENTION

In accordance with the present invention there is provided an injection apparatus for injecting a medicament into a patient, the injection apparatus comprises: (a) a body comprising a stationary head and a movable head that is movable with respect to the stationary head, and (b) a needle attached to a needle holder, the needle holder being held by the movable head and by the stationary head, wherein urging the movable head rearwardly moves a front edge of the needle forwardly with respect to a front face of the movable head. Typically, the movable head is axially movable with respect to the stationary head.

Preferably, the movable head comprises a movable slot, the stationary head comprises a stationary slot, and the movable slot is inclined at a crossing angle with respect to the stationary slot, as seen in a side view of the injection apparatus.

Practically, the crossing angle is in the range of 70° to 110°. Preferably, the movable slot is straight.

If desired, the stationary slot is concave with respect to an imaginary center of curvature of the stationary slot that is located forwardly to the stationary slot. Advantageously, the needle holder comprises an elongated leading pin, the leading pin passes through the stationary slot and through the movable slot, and wherein: rearward movement of the movable head with respect to the stationary head urges a forward movement of the leading pin with respect to the movable slot and a rearward movement of the leading pin with respect to the stationary slot.

Practically, the injection apparatus comprises a pair of stationary slots, a pair of movable slots, and a pair of leading pins, and wherein: the stationary slots, the movable slots and the leading pins are symmetrical with respect to a median plane of the injection apparatus.

Typically, the leading pin has a leading pin length that is larger than a leading pin width, and wherein: the leading pin length is similar to a stationary slot width and slightly smaller therefrom, and, the leading pin width is similar to a movable slot width and slightly smaller therefrom.

Further typically, the injection apparatus comprises a handle for being held by an operator.

Advantageously, the movement of the needle from a retracted position, in an unpressed position of the movable head, to a fully extended position, in a fully pressed position of the movable head, is along a straight line and at a predetermined slant angle with respect to a longitudinal axis of the injection apparatus.

Typically, the slant angle is in the range of 0° to 70°.

Advantageously, the medicament is injected automatically when the needle has reached a predetermined fully extended position.

Still further advantageously, the injection apparatus comprises a dosing chamber, and a piston for pushing the medicament out of the dosing chamber, and wherein the medicament is loaded automatically into the dosing chamber right after the piston has reached a piston forwardmost position.

Practically, the injection apparatus comprises a control panel for administrating various functions of an injection process, and the control panel transmits a real-time information to another device.

Advantageously, the injection apparatus comprises control means for setting and verifying different volumes of a dose to be injected. Typically, the control means are formed from an encoder.

In certain embodiments, the injection apparatus of the invention further comprises at least 2 inlet non-return valves 44, wherein each inlet is connected to a different medicament container. In specific embodiments, the injection apparatus comprises 2, 3, 4, 5, 6, 7, 8, 9, or 10 inlet non-return valves 44, each connected to the same or different container. In a specific embodiment, each one of said inlet non-return valves 44 opens and closes electronically. In yet another specific embodiment, said inlet non-return valves 44 are controlled by a microprocessor.

In certain embodiments of the injection apparatus of the invention the needle being used is a curved needle. Accordingly, in a specific embodiment, the notch which leads said curved needle is also curved such that when the needle comes out of the movable head, the curved needle enters underneath the animal skin without penetrating deeply into the animal muscle or tissue.

BRIEF DESCRIPTION OF THE DRAWINGS

For a better understanding of the present invention and to show how the same may be carried out in practice, reference will now be made to the accompanying drawings, in which.

DESCRIPTION OF PREFERRED EMBODIMENTS

Attention is first drawn to FIGS. 1 to 5 that show an injection apparatus 10 according to the present invention. For a matter of convenience, the injection apparatus will hereinafter be called the "apparatus" 10.

Figure 3:
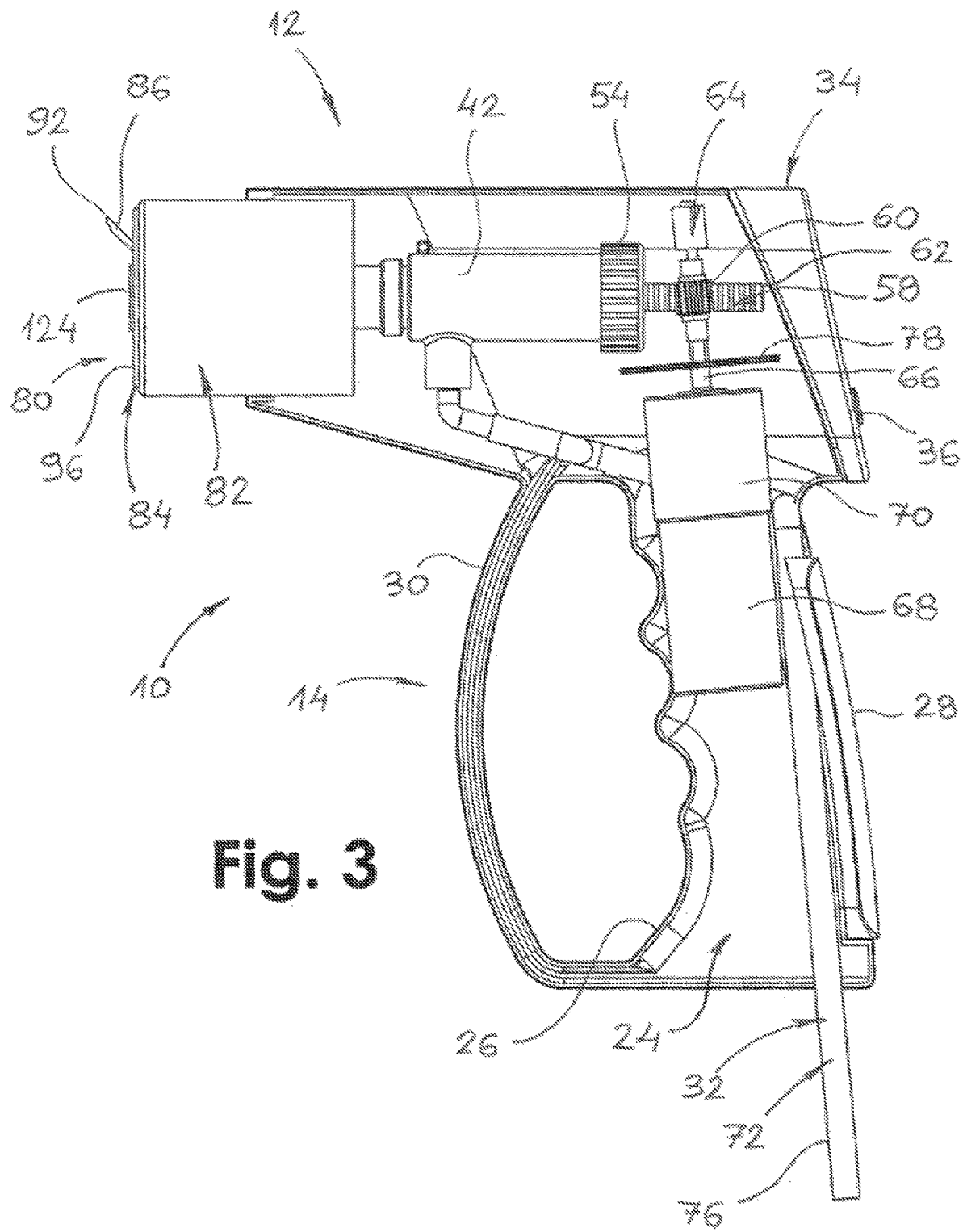
FIG. 3 is a side perspective view of the injection apparatus of FIG. 1 with the left body portion removed.

The apparatus 10 is gun-shaped and comprises a body 12 and a holding portion 14 transversely directed thereto. For the ease of assembly and maintenance, at some cases the body 12 is formed from two separate portions that are connected to each other, namely, a right body portion 16 and a left body portion 18. Similarly, the holding portion 14 is formed from two separate portions that are connected to each other, namely, a right holding portion 20 and a left holding portion 22. At some embodiments, for example, as shown in FIG. 3, the right body portion 16 and the right holding portion 20 are formed as a unitary piece. Similarly, the left body portion 18 and the left holding portion 22 are formed as a unitary piece.

The holding portion 14 comprises a handle 24 having a gripping portion 26 in a forward portion thereof. A safety catch 28 is located in a rear portion of the handle 24. The safety catch 28 prevents accidental injection by the apparatus 10 when it is not properly held by the operator. A hand protector or guard 30 is positioned forwardly to the handle 24. The guard has several functions: (1) protecting the operator's fingers from being hurt, (2) enabling free motion and operation of the operator's fingers without being disturbed, and, (3) serving as a hanger to the injection apparatus 10 when the injection apparatus is not being used.

A medicament conveying pipe 32 for conveying the medicament to be injected enters the handle 24 from a lower side of the handle. The medicament conveying pipe 32 is typically connected to a large bulk medicament container (not shown). The large bulk container is carried by the operator, or, it lays in a location adjacent the operator, so that it could be efficiently being used during the injection process.

It should be noted that directional terms appearing throughout the specification and claims, e.g. "forward", "rear", "upper", "lower" etc., are used as terms of convenience to distinguish the location of various surfaces relative to each other. These terms are defined with reference to the figures, however, they are used for illustrative purposes only, and are not intended to limit the scope of the appended claims.

Figure 1:
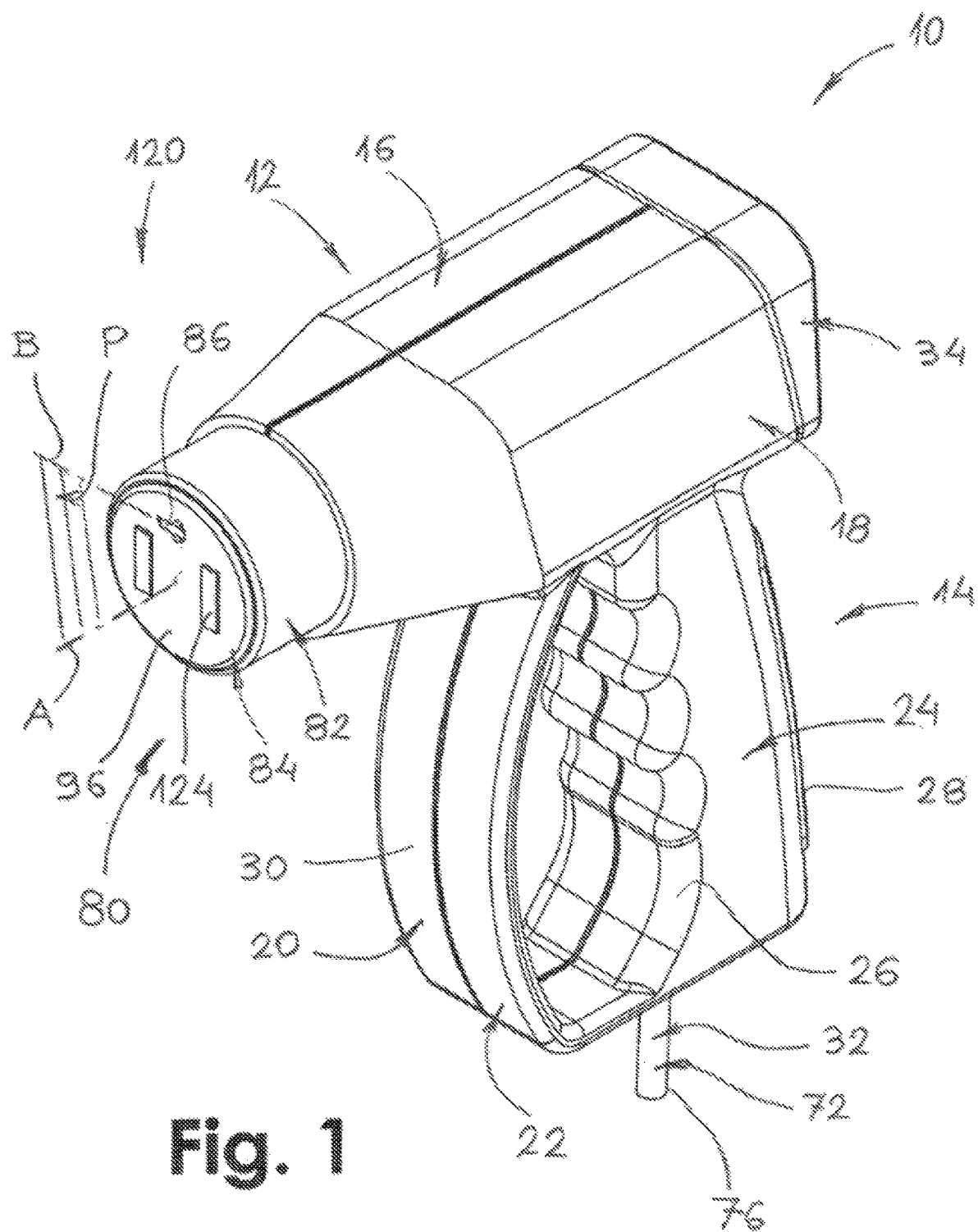
FIG. 1 is a front perspective view of an injection apparatus according to the present invention.
Figure 2:
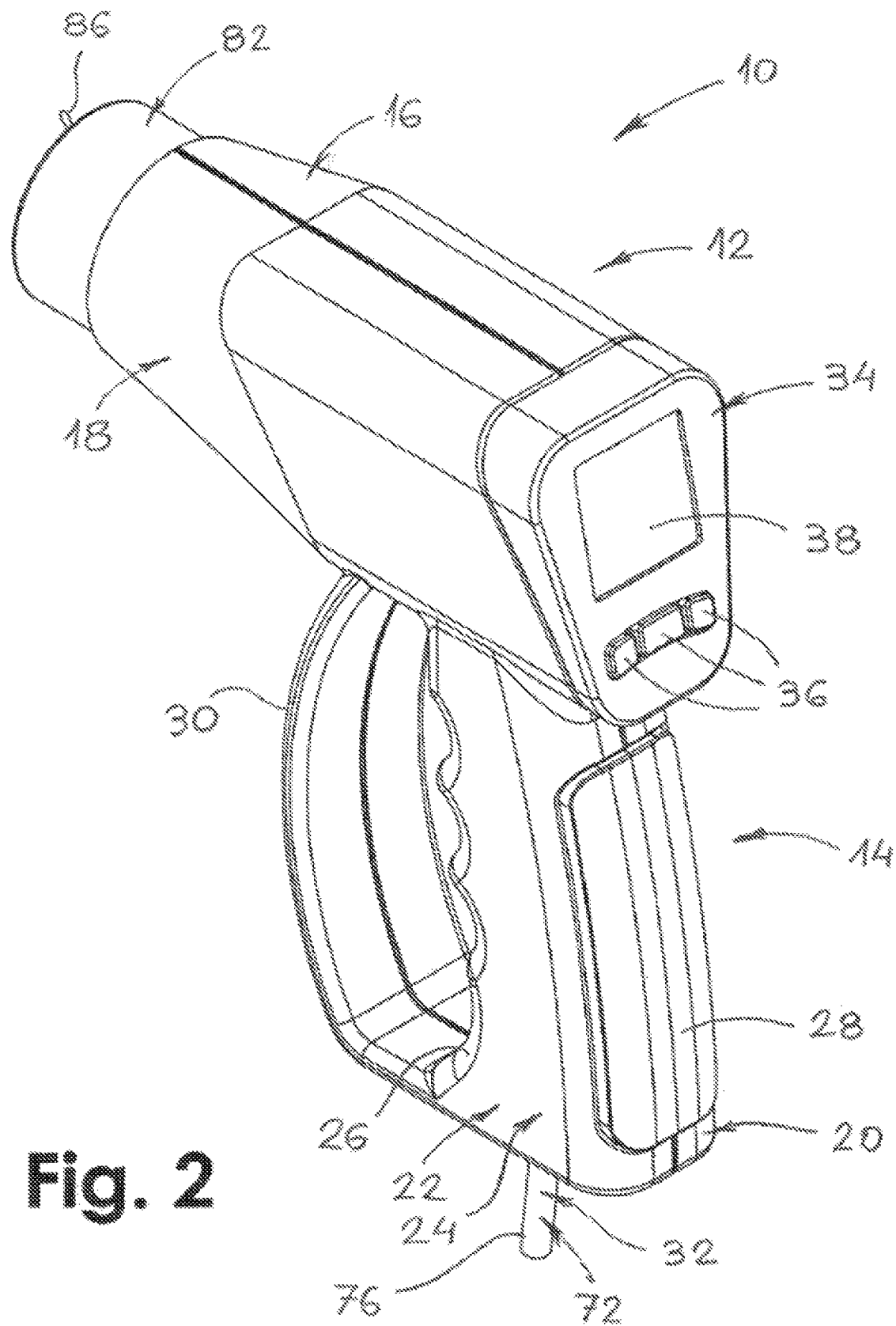
FIG. 2 is a rear perspective view of the injection apparatus of FIG. 1.

As can be clearly seen in FIG. 2, the apparatus 10 is provided with a control panel 34 in a rear portion of the body 12. The control panel 34 comprises operating switches 36 (that, if desired, may be of a "push button" type), for switching between the various functions, and, a screen 38 (or a display) for presenting data and the set functions. The control panel 34 may set and display, but not limited to, the following functions:

1—Number of proper injections
2—Number of faulty injections
3—Amount of accumulated injected medicament
4—Amount of medicament per injection (dosage pre-set adjustment)
5—Rate of injections
6—Intermissions
7—Time of injections (time when each injection took place)
8—Caregiver person (operator) identifying code
9—Date
10—Time
11—Type of medicament
12—Code of farm
13—Code of building within farm
14—Code of poultry enclosure within farm, or of fish pond
15—Code/type of animal
16—Battery status
17—Wireless signal
18—Alert for default
19—General remarks
20—Reports generating
21—Amount of medicament per injection (dosage pre-set adjustment for each container)

The control panel 34 may provide an alarm when faulty conditions occur. For example, in a case when an injection process is interrupted from any reason (e.g., blocked needle, broken piping, end of medicament, faulty motor, stuck piston, lack of signal to the clutch, faulty operation switch, faulty safety catch, etc.), an alarm is turned-on. The alarm may be a visual signal (such as light, blinking light, or the like), an audio signal (such as a buzzer, a siren, or the like), or, a combination of a visual signal and an audio signal.

During the injecting process, the control panel 34 of each of the injection apparatuses 10 (when there is a multitude of apparatuses involved) transmits the relevant information through Bluetooth, Wi-Fi, wire or other means, to a host computer, Smartphone, or the like. Hence, real-time information regarding the injection process can be continuously observed and monitored at a remote location, thus enabling immediate intervening of authorized personnel whenever necessary.

The medicament is conveyed, through the medicament conveying pipe 32 into a dosing chamber 40 of a cylinder 42. The medicament conveying pipe 32 is connected to the dosing chamber 40 through an inlet non-return valve 44. The inlet non-return valve 44 enables medicament flow into the dosing chamber 40 during a "refilling" or "medicament loading" stage, and, prevents return flow of the medicament into the medicament conveying pipe 32 during an "injection" stage. The dosing chamber 40 is limited in a rear portion thereof with a piston head 46 of a piston 48.

The piston head 46 comprises a sealing ring 50 for sealing between the piston head 46 and the cylinder 42. A piston rod 52 extends rearwardly from the piston head 46 and protrudes through a cylinder rear cap 54 that encloses the cylinder 42 at its rear portion. A coil spring 56 is located between the piston head 46 and the cylinder rear cap 54. The coil spring 56 urges the piston head 46 forwardly.

A rear portion of the piston rod 52 comprises a rack 58 that corresponds with a pinion 60 turning thereon. The rack 58 is designed such that in a rearwardmost position of the piston head 46 a rack rear end 62 does not protrude rearwardly from the control panel 34, and, in a forwardmost position of the piston head 46, the rack 58 is still in engagement with the pinion 60.

The pinion 60 is engaged through a clutch assembly 64 to a driving shaft 66. The driving shaft 66 is engaged to an electrical motor 68 through a gear assembly 70. Typically, the gear assembly 70 is a reducing gear, to reduce the revolutions of the electrical motor 68 to the required revolutions at the pinion 60.

According to a preferred embodiment, the electrical motor 68 is a 12V DC motor. The voltage to the electrical motor 68 is supplied from a battery (not shown) that is carried by the operator, and, typically, hanged on the operator's belt. Preferably, the battery is a rechargeable battery.

A supply cable 72 provides power from the battery to the electrical motor 68 and the control panel 34. For a matter of convenience, the supply cable 72 is connected to the medicament conveying pipe 32 at several connection points (not shown) in order to increase safety when using the injection device 10 and preventing the supply cable 72 and the medicament conveying pipe 32 from being accidentally caught by other objects. According to a preferred embodiment, the supply cable 72 and the medicament conveying pipe 32 are bundled together, or, laid together within a single conveying shield 76, thus further increasing the safety of operation of the injection device 10 and ease of its use.

An encoder 78 is assembled on the driving shaft 66. The encoder 78 provides the control panel 34 information regarding the exact actual turn of the electrical motor 68, thereby enabling the operation of the various functions on time, as will be later described.

Figure 6:
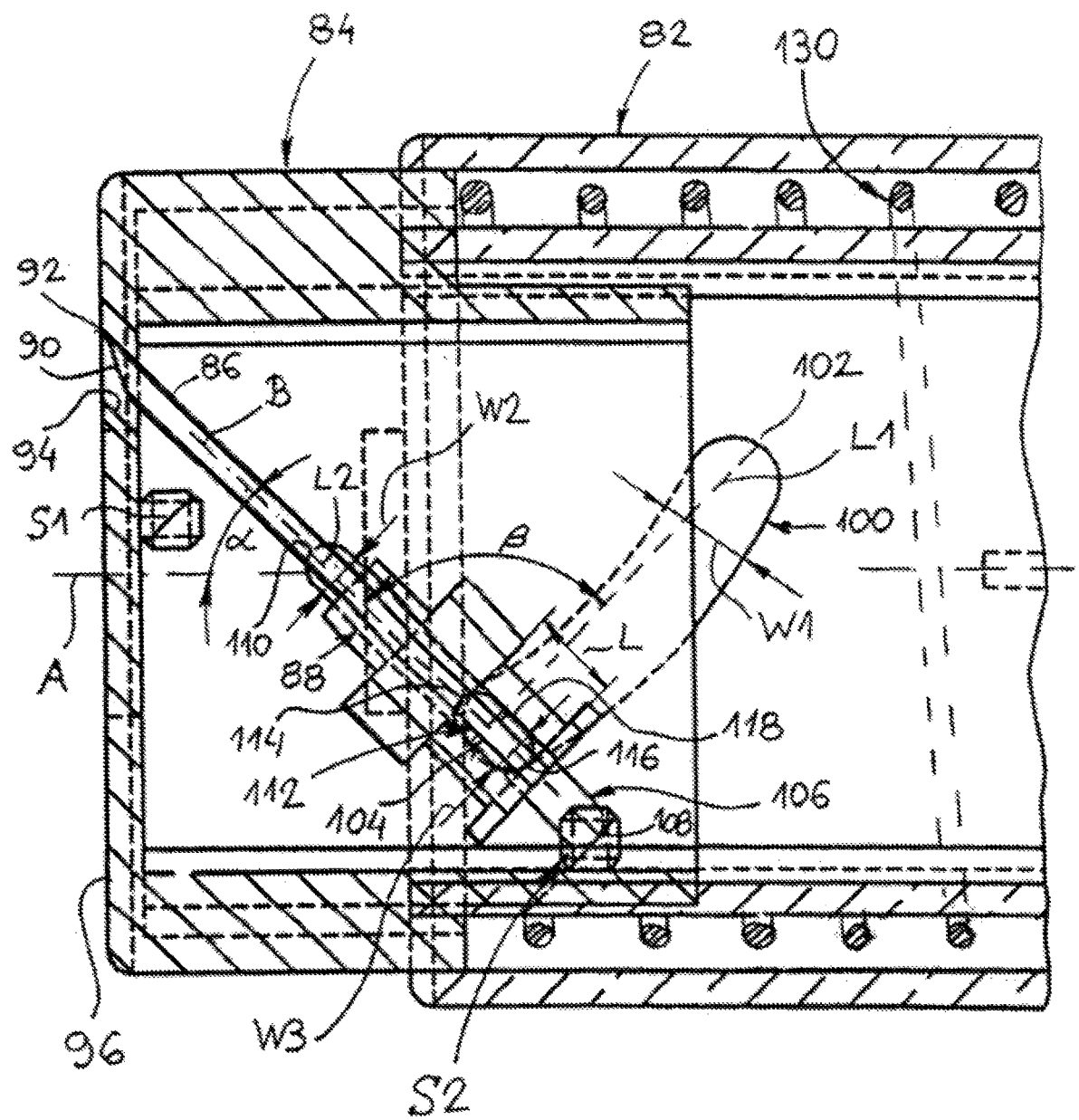
FIG. 6 is a side cross-sectional view of the head assembly with the movable head in an unpressed position.
Figure 7:
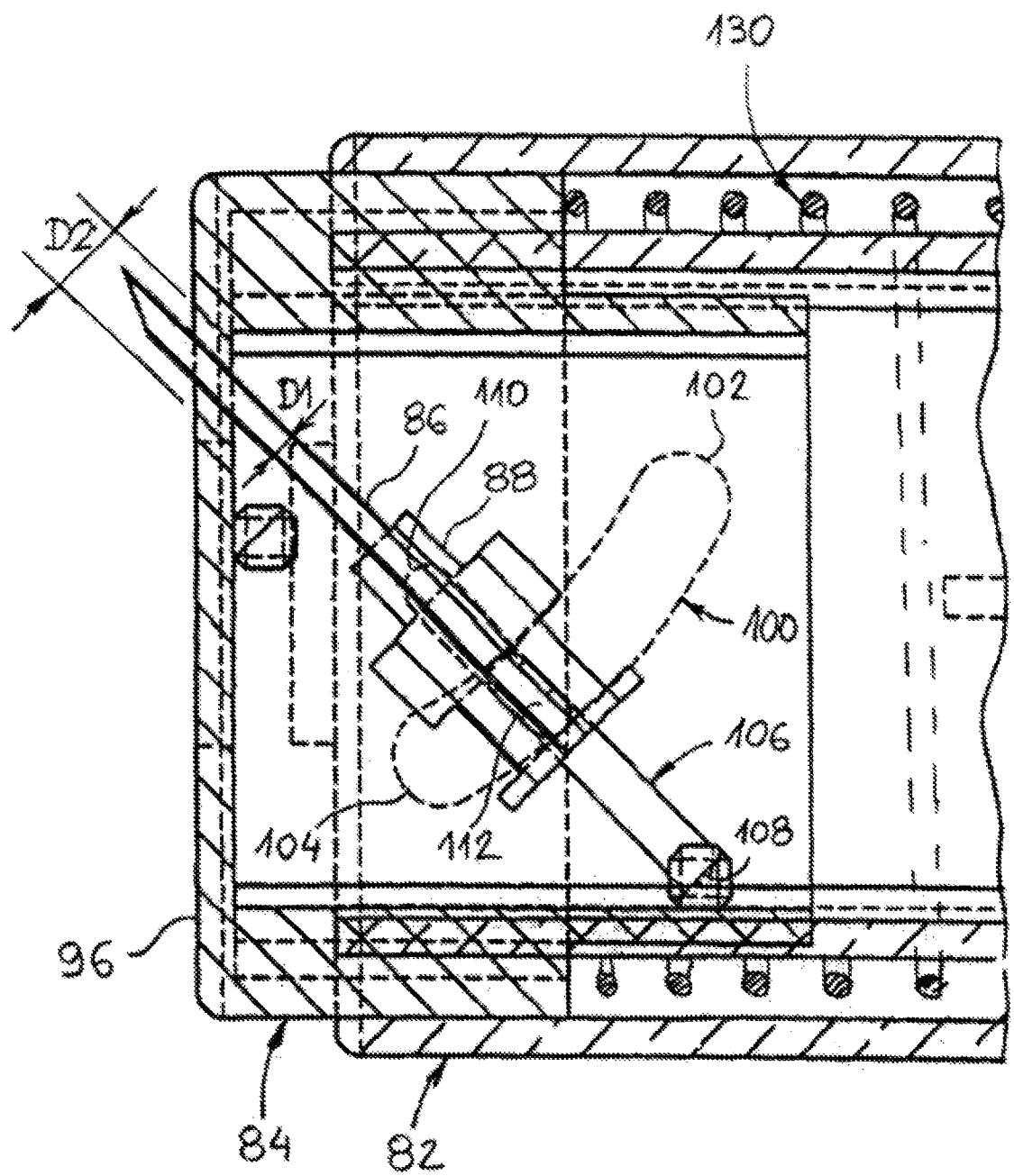
FIG. 7 is a side cross-sectional view of the head assembly with the movable head in an intermediate pressed position.
Figure 8:
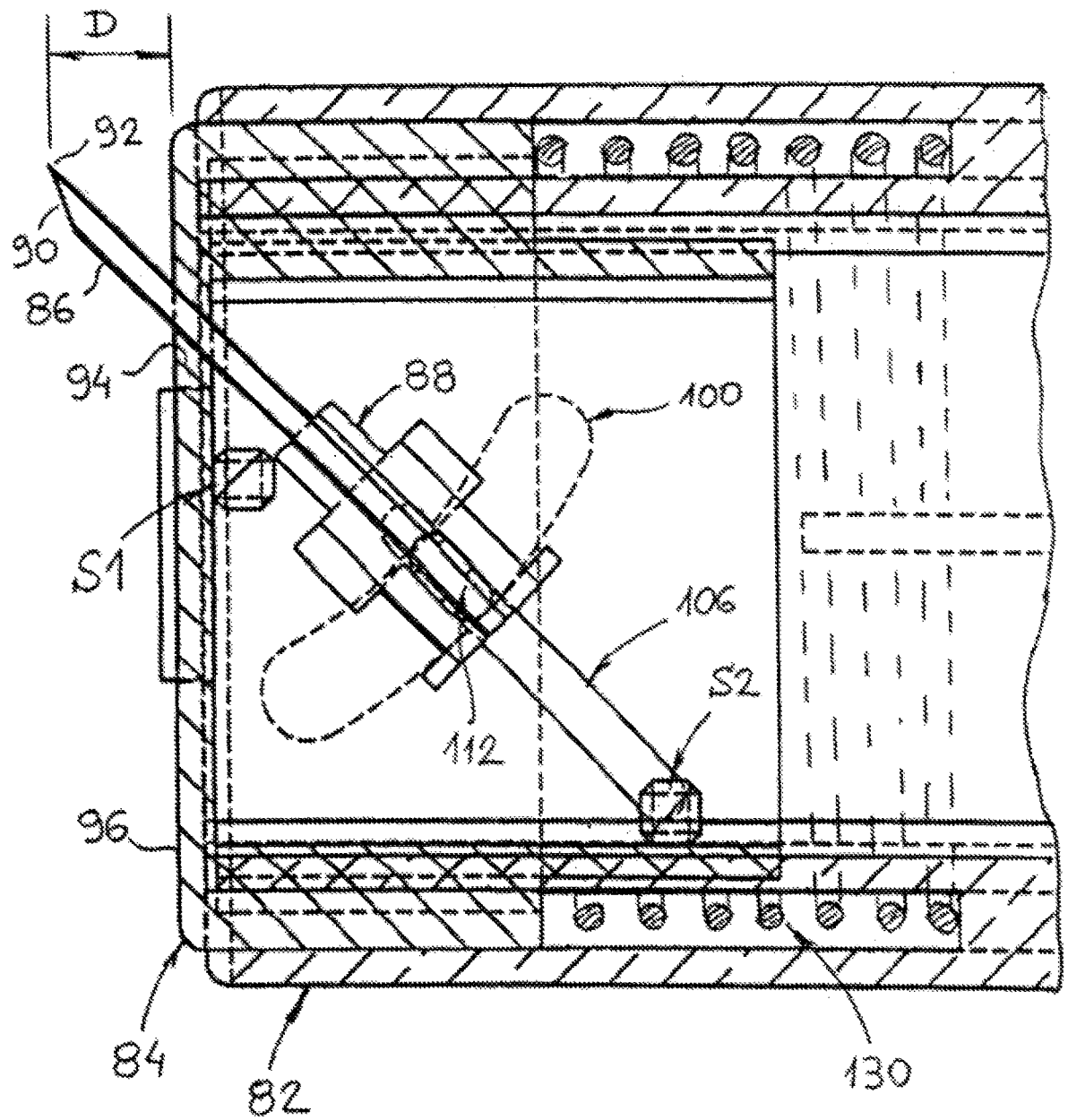
FIG. 8 is a side cross-sectional view of the head assembly with the movable head in a fully pressed position.

Attention is now drawn to FIGS. 6-8. An apparatus front end 80 comprises a stationary head 82 and a movable head 84 that is axially movable with respect to the stationary head 82 along a longitudinal axis A of the injection apparatus 10. Preferably, the longitudinal axis A overlaps a longitudinal axis of the cylinder 42 and the piston 48. According to a specific embodiment of the present invention, the stationary head 82 and the movable head 84 are generally cylindrical.

A needle 86, having a needle diameter D1 and a needle axis B, is fixedly held by a needle holder 88 that is positioned within the stationary head 82 and the movable head 84. The needle 86 is hollow and has a needle opening 90 that is directed oblique with respect to the needle axis B, opens substantially in a forward direction of the injection apparatus 10, and ending with a sharp front edge 92.

The needle axis B is slanted at an acute slant angle α with respect to the longitudinal axis A as seen in a side view of the injection apparatus 10. Typically, the slant angle α is in the range of 0° to 70°. According to a specific embodiment of the present invention, the slant angle α is preferably 45°. In an unpressed position of the movable head 84, the front edge 92 of the needle 86 rests within a needle exit opening 94, having an exit opening diameter D2, and positioned at a point that is rearward to a front face 96 of the movable head 84.

The needle exit opening 94 is directed, like the needle axis B, at the same slant angle α with respect to the longitudinal axis A as seen in a side view of the injection apparatus 10. The exit opening diameter D2 is larger than the needle diameter D1 such that the needle 86 always freely passes through the needle exit opening 94 but also may be supported by it.

Figure 4:
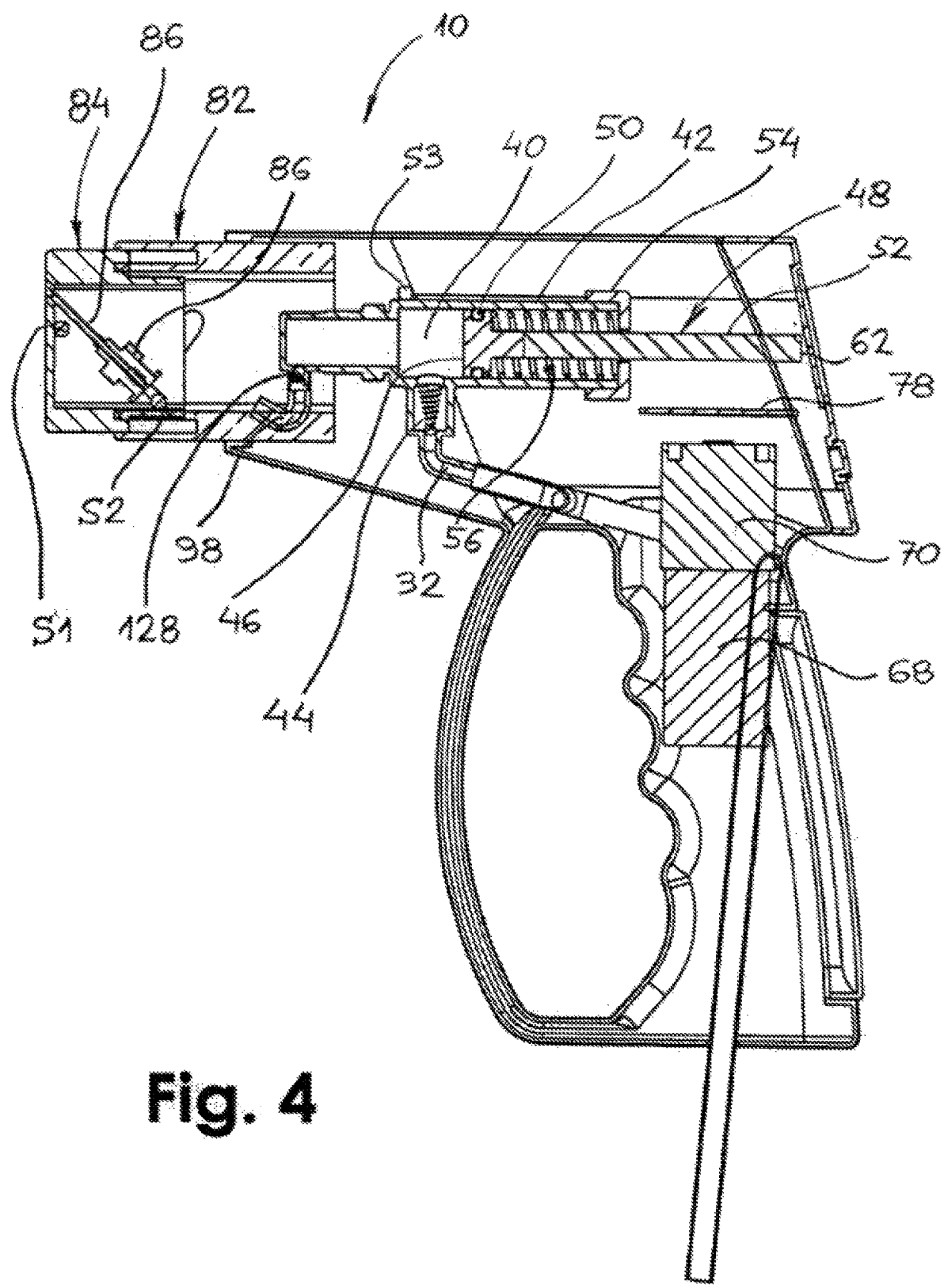
FIG. 4 is a side cross-sectional view of the injection apparatus of FIG. 1 with the piston in its rearward position and the movable head in an unpressed position.
Figure 5:
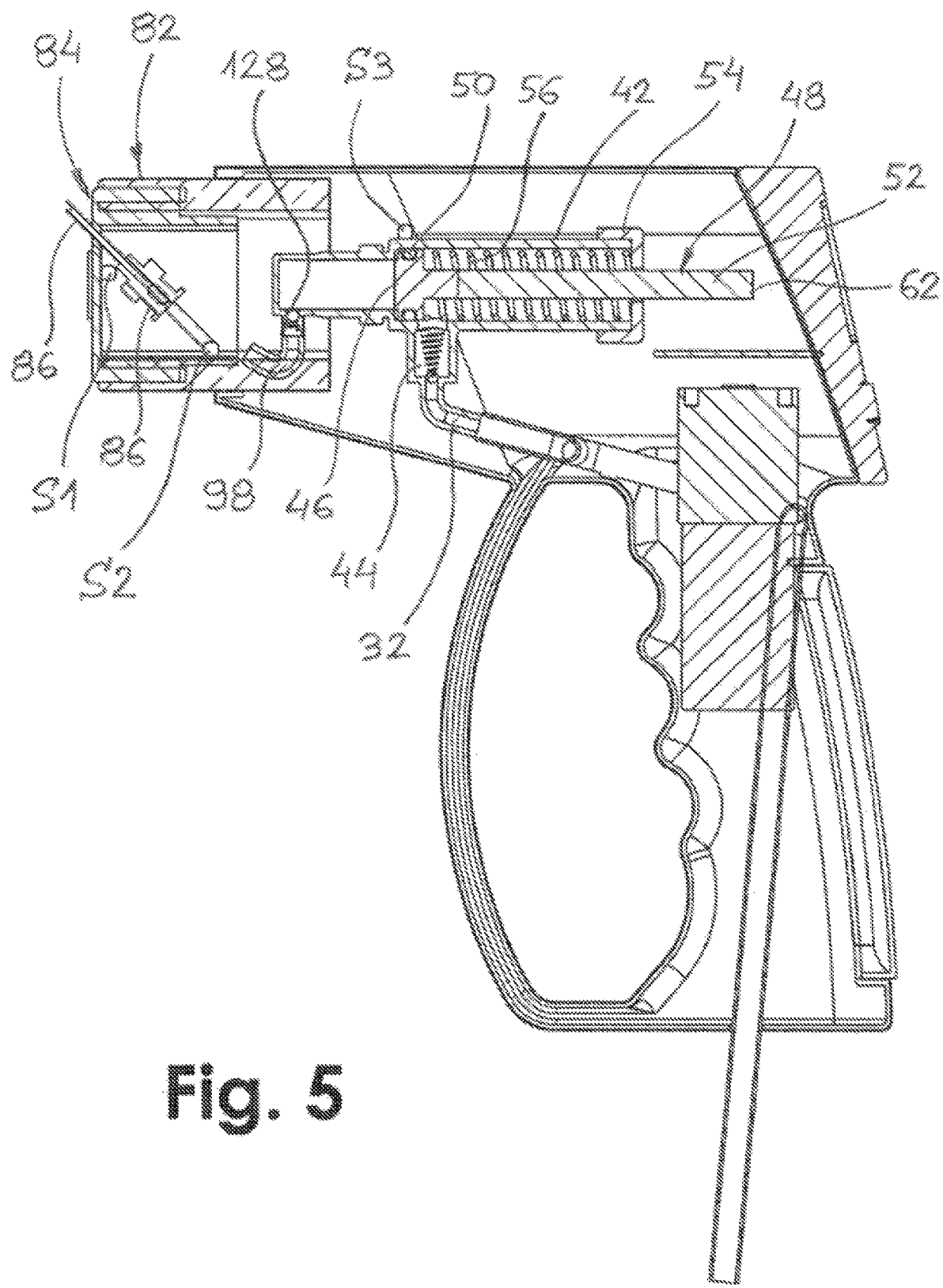
FIG. 5 is a side cross-sectional view of the injection apparatus of FIG. 1 with the piston in its forward position and the movable head in a fully pressed position.

A median plane P of the injection apparatus 10 is defined between the longitudinal axis A and the needle axis B and passes therethrough. A dose conveying pipe 98 connects between a front end of the dosing chamber 40 and a rear end of the needle holder 88. The dose conveying pipe 98 is seen in FIGS. 4 and 5 only in the vicinity of the outlet non-return valve 128 since the rest of the dose conveying pipe 98 is not positioned in the plane shown in these figures, i.e., the median plane P.

The stationary head 82 is provided with a pair of stationary slots 100 that are symmetrical with respect to the median plane P. Each of the stationary slots 100 has a stationary slot width W1 that is constant from a stationary slot rear end 102 to a stationary slot forward end 104. According to a preferred embodiment of the present invention, the stationary slot 100 is concave with respect to an imaginary center of curvature of the stationary slot (not shown) that is located forwardly to the stationary slot 100.

The movable head 84 is provided with a pair of movable slots 106 that are straight, and, symmetrical with respect to the median plane P. Each of the movable slots 106 has a movable slot width W2 that is constant from a movable slot rear end 108 to a movable slot forward end 110.

The movable slot 106 is transversely directed to the stationary slot 100 as seen in a side view of the injection apparatus 10, i.e., when drawing an imaginary first line L1 between a center of the stationary slot rear end 102 and a center of the stationary slot forward end 104, and, an imaginary second line L2 between a center of the movable slot rear end 108 and a center of the movable slot forward end 110, as seen in a side view of the injection apparatus 10, the first line L1 is generally perpendicular to the second line L2, or, forming a crossing angle β therebetween that is typically in the range of 70°-110°, that, as shown in FIG. 6, is measured from the second line L2 to the concave side of the first line L1, when the movable slot forward end 110 and the stationary slot rear end 102 are the vertexes of the measured angle.

The needle holder 88 is provided with a pair of leading pins 112 that are perpendicular to the median plane P and symmetrical with respect thereto. The leading pins 112 are rigidly attached to the needle holder 88 and may form an integral portion thereof. Each of the leading pins 112 has a front arcuate end 114 and a rear arcuate end 116 that are connected by two parallel long sides 118. The maximal distance between the front arcuate end 114 and the rear arcuate end 116 defines a leading pin length L. The distance between the long sides 118 defines a leading pin width W3.

Since the leading pin 112 is provided with long sides 118 further to the front arcuate end 114 and the rear arcuate end 116, the leading pin length L is larger than the leading pin width W3, thus, the leading pin 112 may be described as an "elongated" or "oval" pin. Therefore, since the leading pin 112 is elongated and not round (in a cross-sectional view thereof parallel to the median plane P), it cannot rotate with respect to the movable slot 106. In this way, it is ensured that the leading pin 112, and, hence, the needle 86, will always be at the same angle with respect to the movable head 84 and with respect to the stationary head 82 and the entire injection apparatus 10.

The leading pin width W3 is similar to the movable slot width W2 and slightly smaller therefrom. The leading pin length L is similar to the stationary slot width W1 and slightly smaller therefrom. The leading pin 112, at each side of the median plane P, passes through the adjacent stationary slot 100 and through the movable slot 106.

FIG. 6 shows an unpressed position of the movable head 84. In this position, the front edge 92 of the needle 86 rests within the needle exit opening 94, as mentioned above, and does not protrude forwardly from the front face 96 of the movable head 84. When the movable head 84 starts to be pressed rearwardly, as shown in FIG. 7, it exerts a rearwardly directed force on the leading pin 112. Since the leading pin 112 cannot rotate within the movable slot 106, it is urged to move within the movable slot 106 a forward movement with respect to the movable slot 106.

Thus, as shown in FIG. 7, the leading pin 112 has moved forwardly with respect to the movable slot rear end 108. Now, since the leading pin 112 cannot move forwardly due to the fact that it is limited within the stationary slot 100, it is urged to move within the stationary slot 100, at the same orientation, and away from the stationary slot forward end 104. At this position, the front edge 92 of the needle 86 protrudes forwardly from the front face 96 of the movable head 84. Thus, further pressing rearwardly the movable head 84 further protrudes the front edge 92 of the needle 86 with respect to the front face 96 of the movable head 84, and, simultaneously, the leading pin 112 advances forwardly with respect to the movable slot 106, towards the movable slot forward end 110, and rearwardly with respect to the stationary slot 100, towards the stationary slot rear end 102.

FIG. 8 shows the position of the needle 86 and the needle holder 88 when the movable head 84 is in a fully pressed position. In this position, the needle 86 extends forwardly from the front face 96 of the movable head 84 a maximal protruding depth D. In this position, the injection apparatus 10 is ready to deliver the medicament into the patient. According to the described above, during the entire stroke, i.e., the forward protruding of the needle 86 with respect to the front face 96 of the movable head 84, the needle 86 moves in a straight line, in the same direction, at the same slant angle $\alpha$ with respect to the longitudinal axis A.

The injection apparatus 10 can be used for injecting a medicament into any patient. However, the injection apparatus 10 is specifically designed for being used on animals, and is particularly useful for injecting a large number of individuals such as poultry or fish.

When passing from one poultry enclosure to another, or, when switching between fish ponds, it is a general practice to sterilize the injection apparatus 10. In order to assure a maximal performance of the injection apparatus 10, it is a common practice to replace several components after a given number of injections. According to a specific embodiment of the present invention, a planned maintenance replacement is accomplished after every 2,000 injections being made. During said replacement, the following parts are replaced: (1) stationary head, (2) movable head, (3) needle holder, (4) needle.

Typically, after 100,000 injections, a more thorough periodical maintenance is being done. During this periodical maintenance worn parts are being replaced. The parts that are being replaced may include, but not limited to, the following: (1) cylinder, (2) piston, (3) sealing ring, (4) coil spring, (5) cylinder rear cap, (6) inlet non-return valve, (7) outlet non-return valve, (8) rack, (9) pinion, (10) clutch assembly, (11) driving shaft, (12) encoder, (13) electric motor, (14) gear assembly.

The present embodiment embodies a slant angle $\alpha$ of 45° between the needle axis B and the longitudinal axis A. However, according to other embodiments, other slant angles are used. As mentioned above, the slant angles typically vary in a range from 0° to 70°. However, most typically, the slant angles vary in a range from 30° to 60°. In a case where it is required to use a slant angle different than 45°, an entire head assembly 120 is to be replaced. The head assembly 120 includes the stationary head 82, the movable head 84, the needle holder 88, and the needle 86.

In order to enable proper functioning, the injection apparatus 10 is provided with the following:

1—A "needle out" sensor S1, which senses when the needle 86 had reached its outermost position.

2—A "needle in" sensor S2, which senses when the needle 86 had reached its innermost position.

3—A "piston forward" sensor S3, which senses when the piston 48 had reached its forwardmost position.

4—The encoder 78, which senses the amount of rotation of the electrical motor 68, and, due to the connection to the pinion 60 which rotates on the rack 58, the position of the piston head 46 may be set. This function is useful when it is desired to set different values for the volumes of the medicament to be injected.

Figure 9:
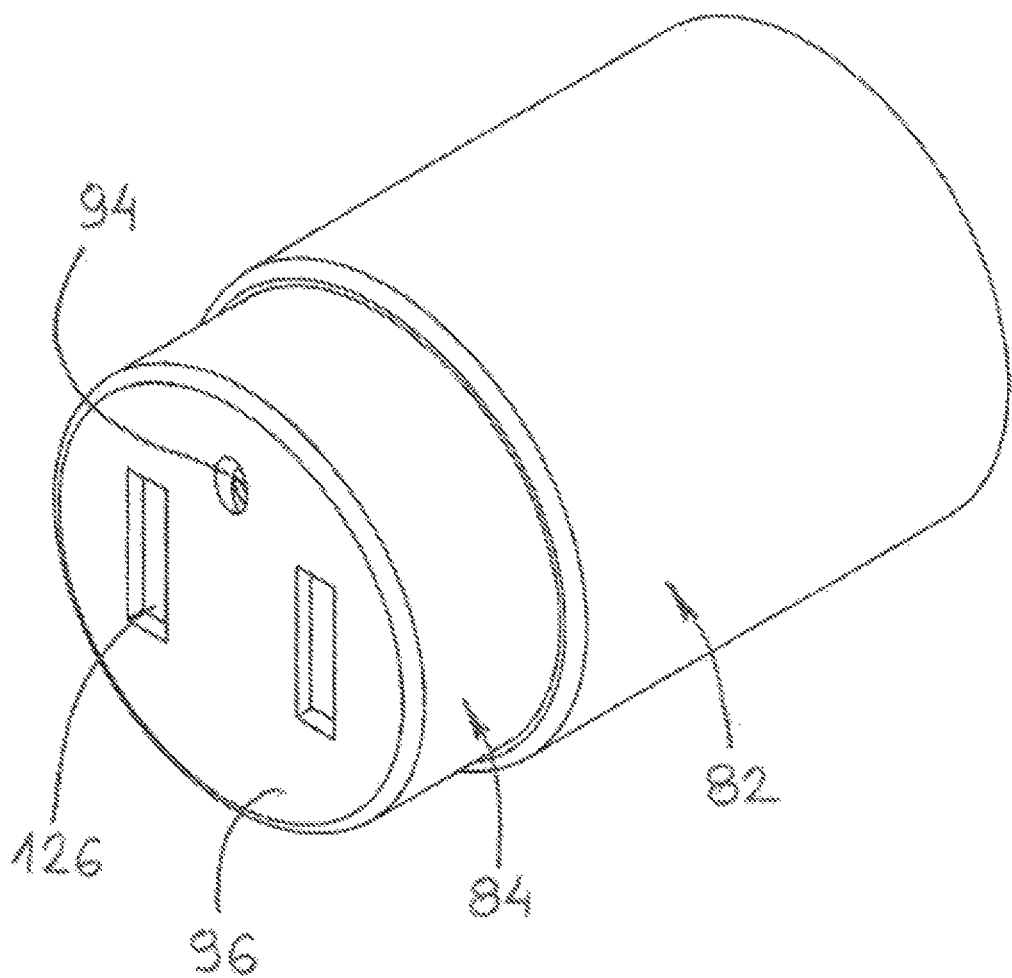
FIG. 9 is a front perspective view of a stamping embodiment of the stationary head and the movable head with the movable head in an unpressed position.
Figure 10:
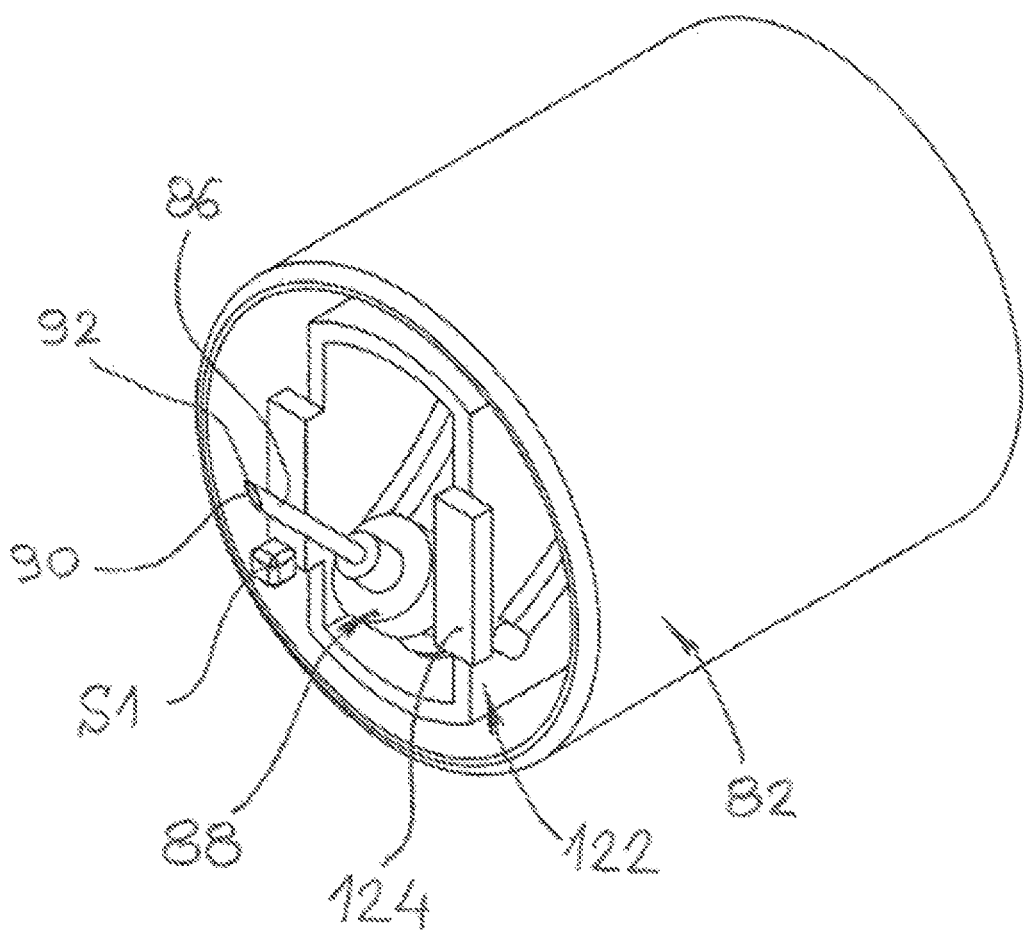
FIG. 10 is a front perspective view of the stationary head of FIG. 9 with the movable head removed.
Figure 11:
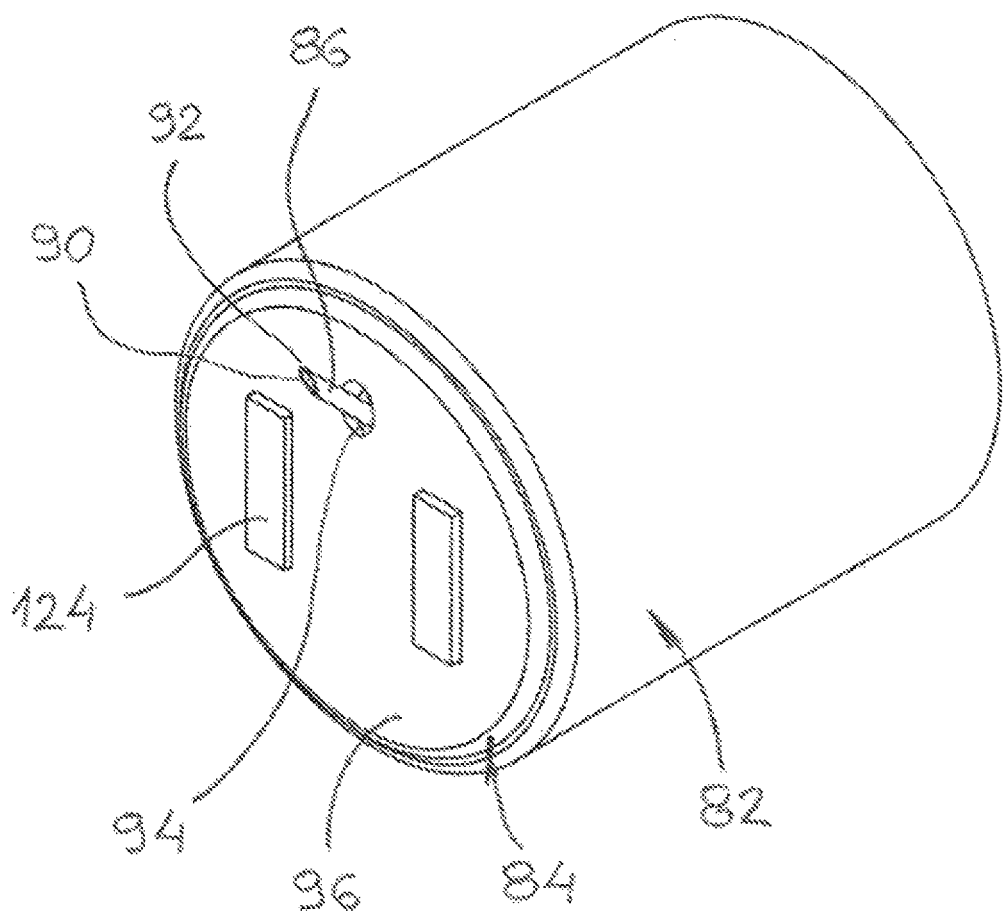
FIG. 11 is a front perspective view of the stationary head and the movable head of FIG. 9 with the movable head in a fully pressed position.
Figure 12:
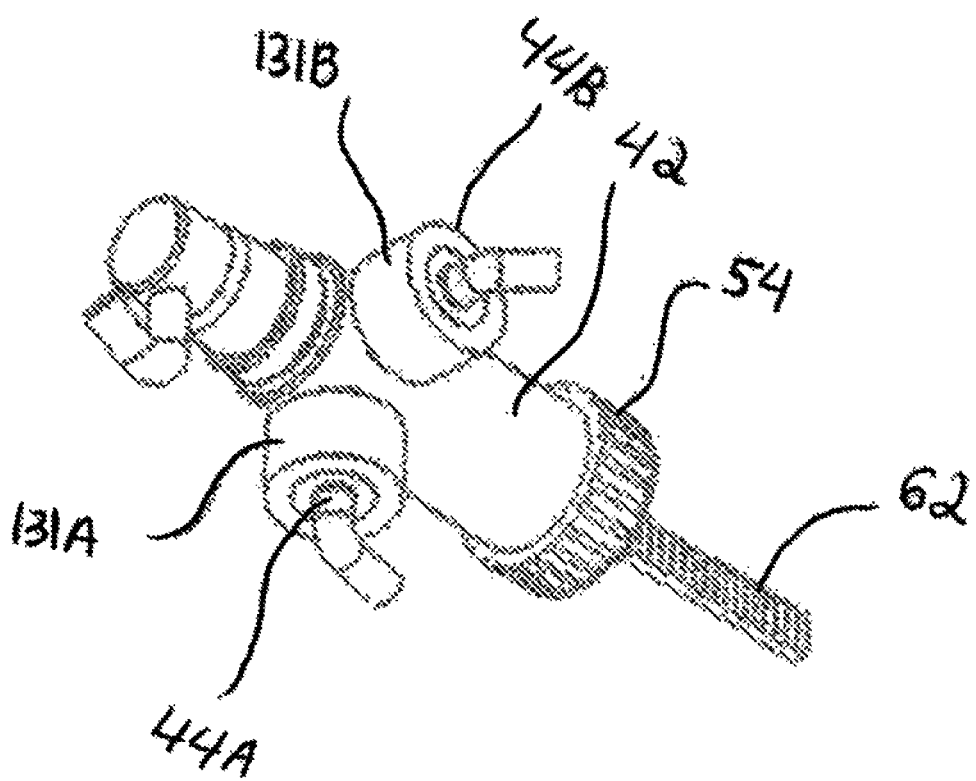
FIG. 12 is a front perspective view of an injection apparatus according to the present invention showing two inlets.
Figure 13:
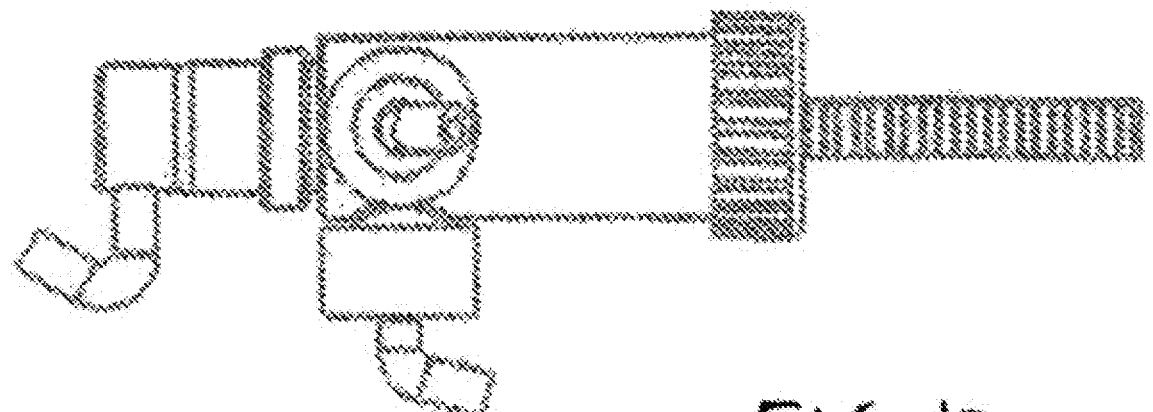
FIG. 13 is a front view of an injection apparatus according to the present invention showing two inlets.
Figure 14:
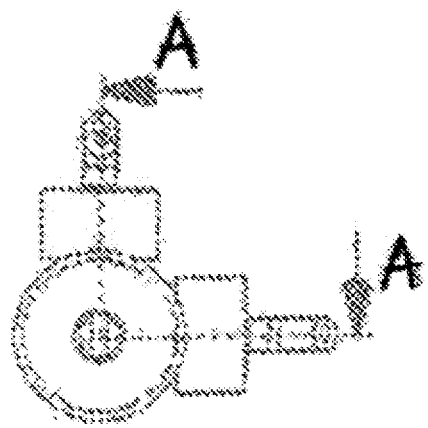
FIG. 14 is a top view of an injection apparatus according to the present invention showing two inlets and a section line.

FIGS. 9-11 show an enlargement of a stamping mechanism 122 of the present invention. The stamping mechanism 122 comprises two rubber or spongy stamps 124 that are symmetrically located at both sides of the median plane P. The stamps 124 have a rectangular shape. The front face 96 of the movable head 84 is provided with two stamping slots 126 that correspond to the stamps 124 and are slightly larger therefrom.

According to some embodiments, the stamps 124 are fixed in place thus constantly facing forwardly. In this case, the stamps 124 receive ink or paint from an ink or paint reservoir through a supply mechanism (not shown). According to other embodiment, the stamps 124 are located on a turning mechanism (not shown). In this case, when the stamps face rearwardly, they abut against an ink pad (not shown), and spread with ink. Now, when the stamps face forwardly, they are ready for stamping the patient.

As shown in FIG. 9, in an unpressed position of the movable head 84, the stamps 124 are rearward to the stamping slots 126 thus not enabling any stamping to be carried out. As shown in FIG. 11, in a fully pressed position of the movable head 84, when the needle 86 has reached its maximal protruding depth D, just in this position the stamps 124 protrude forwardly from the front face 96 of the movable head 84 and stamp against the body of the patient.

Thus, the stamping mechanism 122 enables stamping each patient that has been injected for easy distinguishing thereof comparing to the un-injected patients. However, the stamping mechanism 122 provides "safety stamping", i.e., assuring that only the patients that were injected will be stamped, and any faulty or unintentionally stamping is successfully avoided.

The method of use of the injection apparatus 10 will now be described. The explanation described herein relates to injection to poultry, however, the method is applicable to other animals as well. In a first step, all the required information is set into the control panel 34 by means of the operating switches 36. Then, the operator verifies that the injection apparatus 10 is supplied with the electrical power and the medicament.

At this stage, the injection process may be easily started. The operator holds the injection apparatus 10 with a single hand at the handle 24, and, supports a bird with its other hand. Now, the only operation that the operator has to do is to press the front face 96 of the movable head 84 against the required injection area of the bird. The operator does not have to operate or stress any of his fingers, and, since the handle 24 is grabbed by the operator's hand, the safety catch 28 is pressed thus enabling the functioning of the injection apparatus 10. Thus, as can be appreciated by a man skilled in the art, the injection apparatus 10 is very easy to handle and operate.

When the front face 96 of the movable head 84 is pressed, the needle 86 gradually protrudes outwardly and forwardly with respect to the front face 96, as explained above with respect to FIGS. 6-8, until it reaches its maximal protruding depth D. At this position, the front edge 92 of the needle 86 has reached the required depth under the bird skin, and, the needle opening 90 is directed forwardly into the bird.

At this position, the "needle out" sensor S1 senses that the needle 86 has reached its maximal protruding depth D thus signaling the control panel 34 that an injection stroke may begin. Now, the clutch assembly 64 releases the pinion 60 to rotate freely so that the rack 58, and hence the piston 48, is unlocked.

Now, the piston head 46 is urged forwardly by the coil spring 56 that has been pre-loaded after the previous injection. The piston head 46 compresses the medicament found at the dosing chamber 40 thus pushing it, through an outlet non-return valve 128 and through the dose conveying pipe 98 into the needle 86, and, through the needle opening 90 into the patient. The piston forward sensor S3 signals the control panel 34 that the entire dose had been delivered into the bird, so that another "loading" or "refilling" stroke may begin.

According to some embodiments, after a successful delivery of medicament, the control panel 34 signals a "successful injection". This may take place as a visual signal, e.g., by a blink of a green light, or, as an audio signal, e.g., by a short "beep" sound, or, by a combination of a visual signal and an audio signal.

When the operator releases the pressure of the front face 96 of the movable head 84 against the bird, taking into account that the entire injection process lasts a fraction of a second, the operator puts aside the injected bird and grabs another bird to be injected. When the pressure against the front face 96 of the movable head 84 has ceased, a head spring 130 urges the movable head 84 forwardly with respect to the stationary head 82 until the movable head 84 returns to its initial unpressed position.

During the forward movement of the movable head 84 with respect to the stationary head 82, the needle "retracts" into the movable head 84 until the "needle in" sensor S2 senses that the needle 86 is completely back into the movable head 84 and signals to the control panel 34 that another "injecting" stroke may begin. The purpose of the "needle in" sensor S2 is to assure that the needle 86 has been fully retracted into the movable head 84 before injecting the next bird so that the front edge 92 of the needle 86 will not injure the outer skin of the bird prior to inserting the needle 86 into and under the bird's skin.

Hence, when the piston forward sensor S3 signals the control panel 34 that the entire dose had been delivered into the bird, a new "loading" stroke commences. Thus, the electrical motor 68, through the gear assembly 70, rotates the pinion 60 which turns on the rack 58. Since the driving shaft 66 is fixedly placed in its position, the rack 58 forces to move backwards, and, as being a part of the piston rod 52, the entire piston 48 moves backwards and the piston head 46 presses rearwardly the coil spring 56 which remains loaded for the next injecting stroke. The rearward movement of the piston head 46 provides suction of medicament into the dosing chamber 40 since the outlet non-return valve 128 is closed during the suction stage. Thus, a new dose of medicament is placed into the dosing chamber 40 and ready for being injected. The encoder 78 verifies that the turn of the electrical motor 68 is in conformity with the rearward travel of the piston rod 52 that corresponds to the set volume of the medicament to be injected.

Simultaneously to the injecting process, the stamps 124 protrude outwardly and forwardly from the stamping slots 126, as described above, and stamp the bird to show that it had been injected.

When the operator presses the front face 96 of the movable head 84 against another bird, the process described above is repeated.

Although the present invention has been described to a certain degree of particularity, it should be understood that various alterations and modifications could be made without departing from the spirit or scope of the invention as hereinafter claimed.

For example, the injection apparatus does not have to be provided with a medicament conveying pipe. Alternatively, the injection apparatus is provided with a built-in medicament reservoir for retaining therein the medicament. According to some embodiments, the medicament reservoir is located within the body and/or the holding portion, or, is located above the body or in front of the guard, or, it is a part of the guard. According to some embodiments, the medicament reservoir is refillable. According to other embodiments, the medicament reservoir is exchangeable, thus, when the bulk quantity of medicament within the medicament reservoir is finished, the medicament reservoir is replaced with another reservoir filled with medicament.

The electrical motor does not have to be a 12V DC motor, and, according to other embodiments, the electrical motor is a 24V DC motor, or, a DC motor rated for another voltage.

The electrical motor does not have to be fed from a battery, and, if desired, it may be fed from the mains through a transformer. Furthermore, the electrical motor may be a stepper motor or an AC motor.

The injection apparatus does not have to be provided with a gear assembly. According to other types of motors, the speed obtained by the motor is the same speed that corresponds to the speed of the driving shaft.

In other embodiments, the piston is moved through a worm gear, thus preventing the need of a gear assembly. In this case, the electrical motor is connected, through the driving shaft, to a worm of a worm gear. The worm is connected to a worm wheel having an axis of rotation that substantially overlaps with the longitudinal axis of the injection apparatus. An inner portion of the worm wheel rotates, through a clutch (which is typically magnetic or mechanical), a threaded portion of the piston rod. Thus, the electric motor effectively moves the piston rod through a "two-stage" reducing mechanism during the "loading" stroke, and, the piston rod is disengaged from the rotating mechanism so that it could freely move forwardly during the "injection" stroke by the forwardly urging force applied by the coil spring on the piston head.

The stationary head and the movable head do not have to be cylindrical and other shapes that enable their relative axial motion may be applied. For example, the stationary head and the movable head may have an oval or a square cross-section.

The stationary slot does not have to be curved and it may be straight.

The injection apparatus is not always provided with the stamping embodiment as described above and according to other embodiments the head assembly is not provided with a stamping mechanism.

The driving shaft may be perpendicular to the longitudinal axis, or, may be slanted with respect to a perpendicular line to the longitudinal axis, as seen in a side view of the injection apparatus.

The stamps do not have to be formed from rubber or sponge and other known stamps may be similarly applicable. The stamps do not have to be rectangular and any other shape may be used. Furthermore, the stamps do not have to be similar and each stamp may have a different shape.

The stamping mechanism do not have to include two stamps and any other number of stamps may be used, e.g., one, three, or more. The stamps are typically of the same stamping color, however, if desired, different stamps may use different colors.

According to other embodiments, the injection apparatus is not held by an operator hand and is fixed to a fixed object, e.g., a table, a wall, or a frame. In this case, the safety catch is override, or, operated by a foot pedal. In order to operate the injection apparatus in this case, a bird is brought in front of the movable head until it presses it. In this mode, the operator may catch and move a bird by both of his hands. Furthermore, if desired, the operator may hold a bird in each of his hands thus speeding up the speed of injecting by injecting alternatively a bird by each hand.

Attention is now drawn to FIGS. 12-17, which represent yet another embodiment of the invention. In this embodiment, the cylinder 42 has two inlets 44A and 44B. Each of these inlets has a solenoid valve 131A and 131B. These valves are electronically controlled and can open and close the inlets. The inlets are connected to two separate containers (not shown) which contain different medicament.

In some cases it is desirable to give the animal more than one medicament when each of them is prescribed in different doses. In this case the operator loads each container with a different medicament and sets the controller accordingly.

During the loading stage, only one of the inlet valves will open till the piston head 46 reaches a certain location set by the operator, and then this valve closes and the second valve opens until the piston head reaches its final position.

The piston head location can be detected and controlled using the encoder 78.

Figure 15:
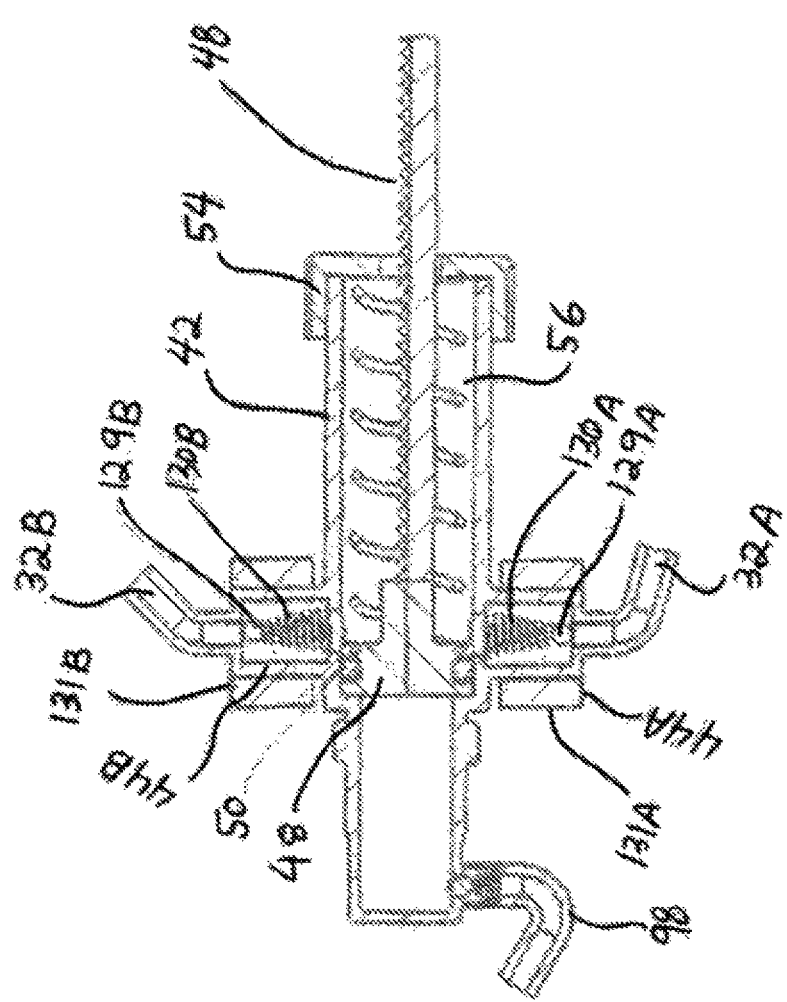
FIG. 15 is a cross sectional view of FIG. 14.

As seen in FIG. 15, the piston head is located at its forward most location and the cylinder is empty. Both inlet valves 131A and 131B are closed.

Figure 16:
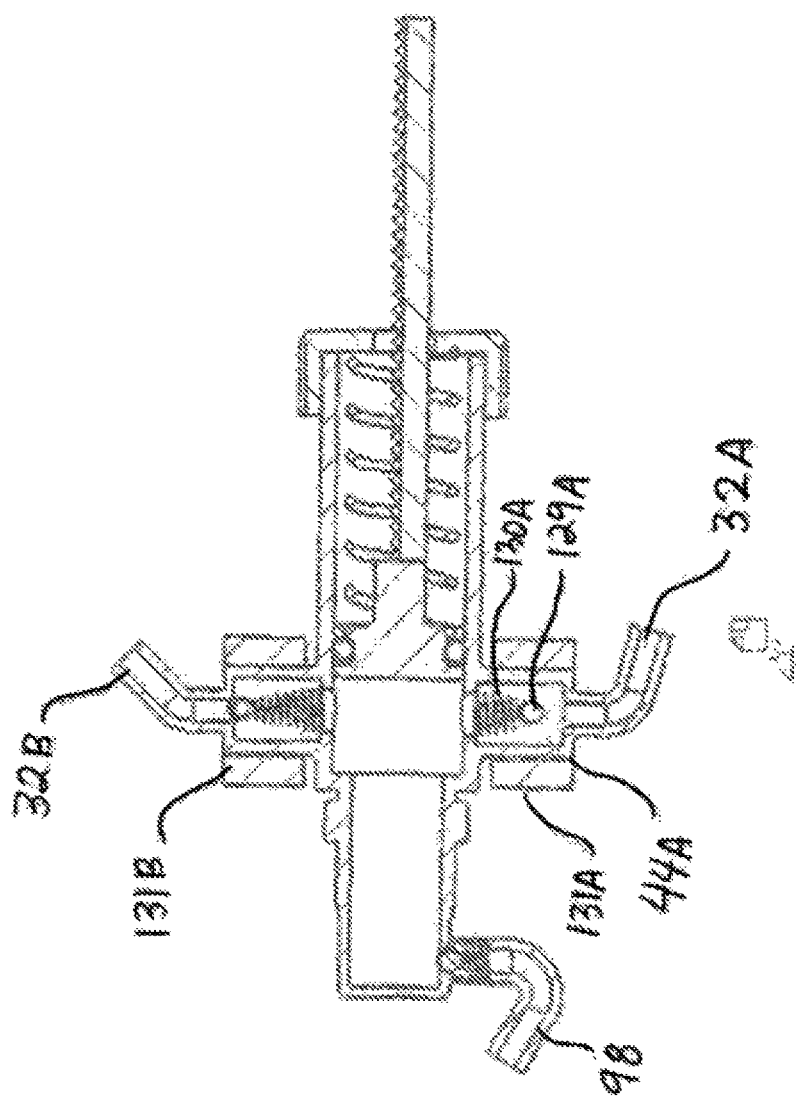
FIG. 16 is a cross sectional view of FIG. 14 showing one valve Open and second valve closed.

As seen in FIG. 16, when the motor starts moving, the piston 48 refills the cylinder, only inlet valve A 44A is opened by activating the solenoid A 131A, and letting only the medicament from container A (not shown) enter the cylinder.

Figure 17:
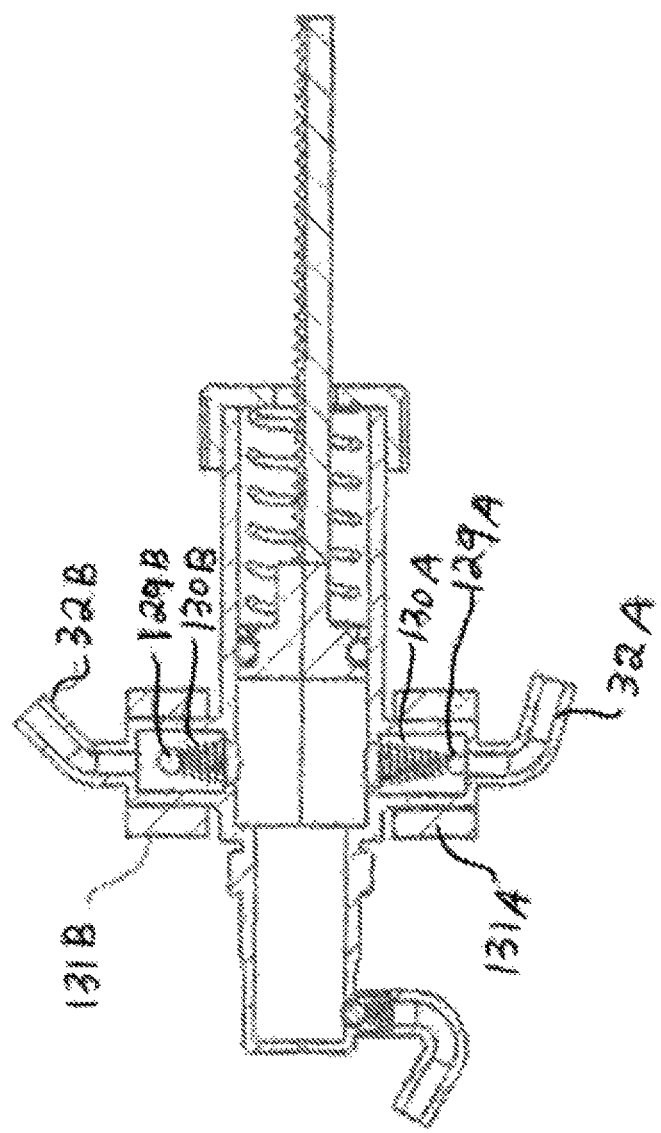
FIG. 17 is a cross sectional view of FIG. 14 showing the second valve Open and the 1st valve closed

As seen in FIG. 17, at the desired location of the cylinder head, the 1st inlet valve closes and the $2^{nd}$ valve opens by activating the solenoid B 131B and deactivating solenoid A 131A.

The cylinder keeps moving backward and the $2^{nd}$ medicament fills the cylinder up to the setup location. Now the cylinder contains two different medicaments. During the injection stage, the cylinder moves forward via the spring 56 and pushes all medicaments through the outlet non-return valve 128 while both inlet valves 131A and 131B are closed.

Figure 18:
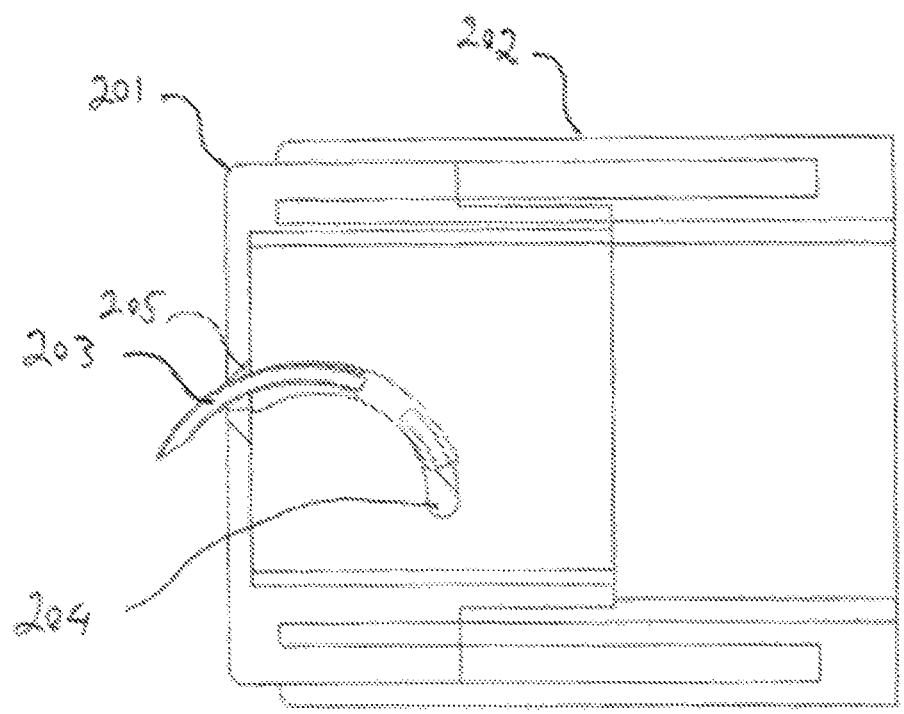
FIG. 18 is a section view of another embodiment of the same invention: The Needle is curved and the Movable Head has a curved notch.
Figure 19:
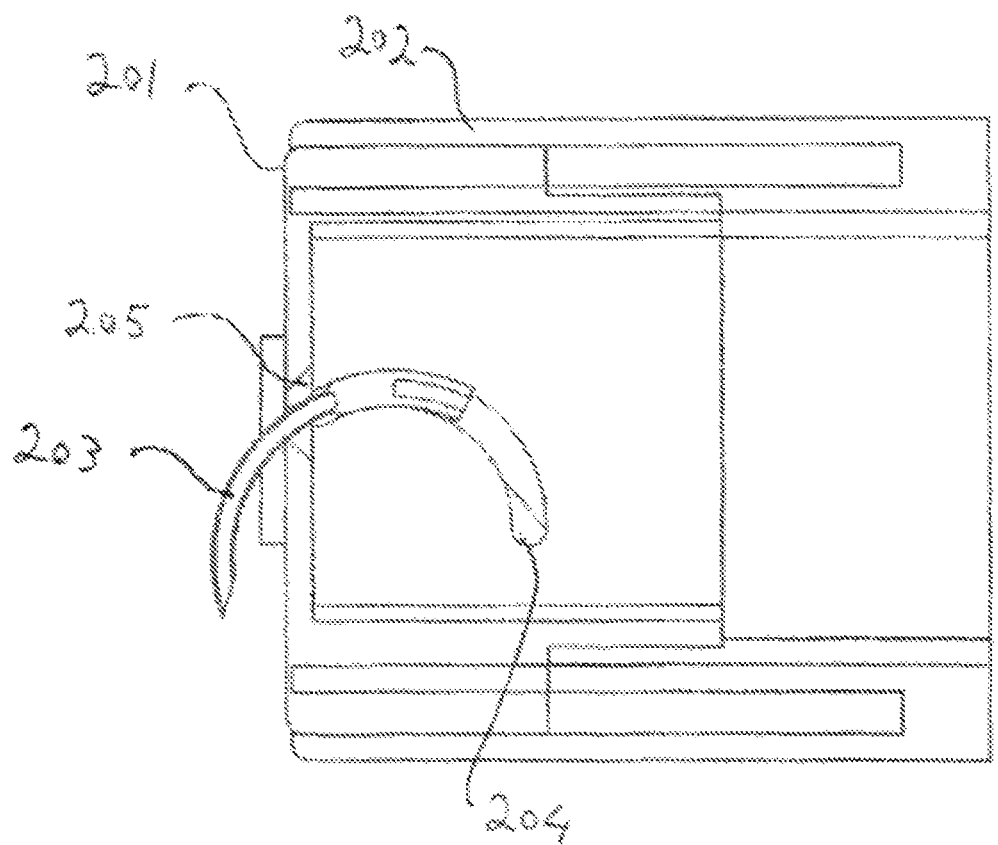
FIG. 19 is a section view of the embodiment with a curve needle. The Movable Head is retracted all the way so the needle is fully extracted.
Figure 20:
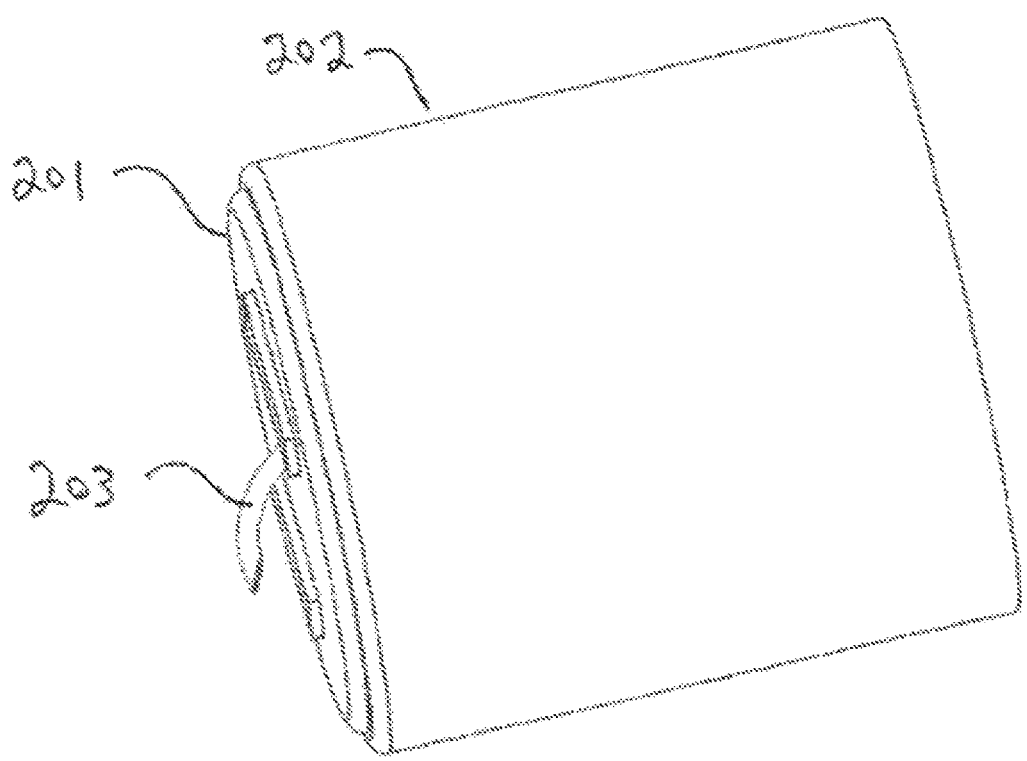
FIG. 20 is an isometric view of the same embodiment with a curved needle.

As seen in FIGS. 18-20, the needle 203 is curved; the notch 204 is also curved accordingly so when the movable head 201 is moved backwards, the needle slides inside the notch 204 and comes out of the hole 205 into the animal body. Because of its shape, the needle enters under the animal skin and does not penetrate the muscles or other tissue of the animal.

The invention claimed is:

1. An injection apparatus, comprising:
a hand-held unit comprising a gripping portion, a stationary head, a movable head at least a portion of which extends distally past the stationary head, and a needle, wherein the movable head is axially movable with respect to the stationary head and wherein the movable head extends over the needle when the movable head is in an extended configuration;
a dosing chamber fluidly coupled to the needle of the hand-held unit, the dosing chamber comprising a first non-return valve and a second non-return valve; and
one or more medicament containers fluidly coupled to the dosing chamber by one or more flexible connecting tubes.

2. The injection apparatus of claim 1, wherein the movable head is movable between the extended configuration and a retracted configuration, wherein when the movable head is in the extended configuration a distal point of the needle is disposed within the movable head, and wherein when the movable head is in the retracted configuration the distal point of the needle is exposed.

3. The injection apparatus of claim 2, further comprising a biasing member configured to bias the movable head into the extended configuration.

4. The injection apparatus of claim 3, wherein the biasing member is a spring.

5. The injection apparatus of claim 1, wherein the first non-return valve allows fluid to flow from the one or more medicament containers into the dosing chamber, and wherein the second non-return valve allows fluid to flow from the dosing chamber to the needle.

6. The injection apparatus of claim 1, wherein the dosing chamber comprises a piston configured to push a medicament out of the dosing chamber.

7. The injection apparatus of claim 6, wherein the piston is operatively coupled to a motor to actuate the piston.

8. The injection apparatus of claim 7, wherein the piston comprises a toothed member, and wherein the injection apparatus further comprises a motor having a correspondingly toothed gear portion configured to engage the toothed member and thereby actuate the piston.

9. The injection apparatus of claim 1, further comprising an encoder configured to control a volume of medicament in the dosing chamber.

10. The injection apparatus of claim 9, wherein the encoder controls the motor and thereby control the position of the piston within the dosing chamber.

11. The injection apparatus of claim 1, further comprising a power source remote from the hand-held unit and operatively coupled thereto via a power cable.

12. The injection apparatus of claim 11, wherein the power source is worn by a user.

13. The injection apparatus of claim 1, wherein medicament is injected automatically upon insertion of the needle to a selected depth within a patient.

14. The injection apparatus of claim 1, further comprising a control panel configured to display information relating to an injection process.

15. The injection apparatus of claim 14, wherein the control panel provides an alarm when the injection process is interrupted.

16. The injection apparatus of claim 14, wherein the control panel can transmit real-time data related to the injection process to a remote location.

17. A method, comprising:
providing an injection apparatus according to claim 1; and
using the apparatus.

18. The method of claim 17, wherein using the apparatus comprises:
pressing the movable head against a body of a patient at an injection location such that the movable head moves rearwardly relative to the stationary portion and a distal edge portion of the needle is exposed; and
administering a medicament to one or more patients using the injection apparatus.

19. The method of claim 18, wherein administering the medicament to the patient comprises automatically injecting a dose of medicament when the needle reaches a selected depth within the patient.

20. The method of claim 18, further comprising using the apparatus to administer medicament to one or more additional patients.

* * * * *